United States Patent
Wang et al.

(10) Patent No.: US 11,534,102 B2
(45) Date of Patent: Dec. 27, 2022

(54) METHOD FOR MEASURING CORPUS CALLOSUM VOLUME OF FETUS BY MEANS OF MAGNETIC RESONANCE IMAGING, AND MAGNETIC RESONANCE IMAGING APPARATUS

(71) Applicants: Siemens Healthineers Ltd., Shanghai (CN); Shandong Medical Imaging Research Institute, Jinan (CN)

(72) Inventors: Guangbin Wang, Shandong (CN); Tian Yi Qian, Beijing (CN); Xin Chen, Shandong (CN); Cong Sun, Shandong (CN)

(73) Assignees: Siemens Healthcare GmbH, Erlangen (DE); Shandong Medical Imaging Research Institute, Shandong (CN)

( * ) Notice: Subject to any disclaimer, the term of this patent is extended or adjusted under 35 U.S.C. 154(b) by 296 days.

(21) Appl. No.: 16/858,141

(22) Filed: Apr. 24, 2020

(65) Prior Publication Data

US 2020/0337626 A1  Oct. 29, 2020

(30) Foreign Application Priority Data

Apr. 26, 2019 (CN) .......................... 201910345653.6

(51) Int. Cl.
*G06V 10/00* (2022.01)
*A61B 5/00* (2006.01)
(Continued)

(52) U.S. Cl.
CPC ............ *A61B 5/4064* (2013.01); *A61B 5/055* (2013.01); *G01R 33/56341* (2013.01);
(Continued)

(58) Field of Classification Search
CPC ... A61B 5/4064; A61B 5/055; A61B 2503/02; A61B 5/0042; A61B 5/4362;
(Continued)

(56) References Cited

U.S. PATENT DOCUMENTS

| 11,026,626 B2* | 6/2021 | Varkuti ..................... G06T 7/74 |
| 2008/0205733 A1* | 8/2008 | Laidlaw ............... A61B 5/4064 |
| | | 382/131 |

(Continued)

OTHER PUBLICATIONS

G Malinger and H Zakut, "The corpus callosum: normal fetal development as shown by transvaginal sonography", American Journal of Roentgenology 1993 161:5, 1041-1043 (Year: 1993).*

(Continued)

*Primary Examiner* — Van D Huynh
(74) *Attorney, Agent, or Firm* — Banner & Witcoff Ltd.

(57) ABSTRACT

Techniques are disclosed for measuring the corpus callosum volume of a fetus using magnetic resonance imaging. A scanogram of a fetus is acquired, and a detection area is determined using the corpus callosum position of the fetus in the scanogram. Magnetic resonance scanning is performed on the detection area to obtain a diffusion weighted image, with a gradient direction that is orthogonal or normal to an extending direction of fiber bundles of the corpus callosum. A fetal head image is cropped in the diffusion weighted image, and a predetermined threshold is applied to obtain an image including pixels having a brightness value that is greater than the threshold. Image processing is performed on the binarized image, with the largest region therein being identified as the corpus callosum, and the sum of voxel dimensions associated with the signal of the largest region being calculated as the corpus callosum volume.

17 Claims, 4 Drawing Sheets

(51) Int. Cl.
  *A61B 5/055*    (2006.01)
  *G01R 33/563*   (2006.01)
  *G06N 20/00*    (2019.01)
  *G06V 10/40*    (2022.01)
  *G06V 10/46*    (2022.01)

(52) U.S. Cl.
  CPC ............. *G06N 20/00* (2019.01); *G06V 10/40* (2022.01); *A61B 2503/02* (2013.01); *G06V 10/467* (2022.01)

(58) Field of Classification Search
  CPC ............ A61B 5/7267; A61B 2576/026; G01R 33/56341; G01R 33/5616; G06N 20/00; G06N 3/08; G06V 10/40; G06V 10/467; G06V 2201/03; G06V 10/25; G06V 10/28; G06V 10/50
  USPC .......................................................... 600/300
  See application file for complete search history.

(56) References Cited

U.S. PATENT DOCUMENTS

| | | | |
|---|---|---|---|
| 2011/0199084 A1* | 8/2011 | Hasan | G06T 1/00 324/309 |
| 2014/0288004 A1* | 9/2014 | Wang | A23L 33/40 514/17.7 |
| 2014/0314298 A1* | 10/2014 | Fieremans | G06T 7/0012 382/131 |
| 2015/0253410 A1* | 9/2015 | Warfield | G01R 33/5602 324/309 |
| 2016/0018504 A1* | 1/2016 | Magin | A61B 5/055 324/309 |
| 2016/0098832 A1* | 4/2016 | Yoo | G06T 7/20 382/131 |
| 2016/0166192 A1* | 6/2016 | Lepore | A61B 5/055 600/410 |
| 2016/0196644 A1* | 7/2016 | Peng | G01R 33/5602 382/131 |
| 2018/0185003 A1* | 7/2018 | Zou | A61B 8/0816 |

OTHER PUBLICATIONS

J.H. Harreld, R. Bhore, D.P. Chason and D.M. Twickler, C"orpus Callosum Length by Gestational Age as Evaluated by Fetal MR Imaging", American Journal of Neuroradiology Mar. 2011, 32 (3) 490-494; DOI: https://doi.org/10.3174/ajnr.A2310 (Year: 2011).*

* cited by examiner

METHOD FOR MEASURING CORPUS CALLOSUM VOLUME OF FETUS BY MEANS OF MAGNETIC RESONANCE IMAGING, AND MAGNETIC RESONANCE IMAGING APPARATUS

CROSS-REFERENCE TO RELATED APPLICATIONS

The present application claims the benefit of the filing date of China patent application no. 201910345653.6, filed on Apr. 26, 2019, the contents of which are incorporated herein by reference in their entirety.

TECHNICAL FIELD

The present disclosure relates to techniques for measuring the corpus callosum volume of a fetus by means of magnetic resonance imaging, and in particular to a method for automatically measuring the corpus callosum volume of a fetus and a magnetic resonance imaging (MRI) apparatus.

BACKGROUND

The corpus callosum is a fiber bundle plate composed of fibers that connect the left and right cerebral hemispheres of the brain. Agenesis of the corpus callosum may cause mild mental retardation, mild visual impairment, or contralateral tactile localization disturbance. Therefore, performing screening for abnormalities of the corpus callosum during the fetal period and taking appropriate measures can reduce the probability of neonatal abnormalities.

At present, ultrasonic images are typically used to perform fetal screening. However, screening for abnormalities of the corpus callosum by means of ultrasonic images has high requirements on the experience and techniques of operators. In addition, the volume of the corpus callosum cannot be calculated precisely based on the ultrasonic images, which in turn cannot provide an effective basis for determination by a sonographer. As a result, at present, the abnormalities of the corpus callosum of fetuses cannot be easily determined based on ultrasonic images.

Moreover, at present, abnormalities of the corpus callosum can be detected by means of magnetic resonance imaging for adults. But for a fetus, since it is usually in an active state in a maternal body, it is difficult to perform magnetic resonance imaging. This is because magnetic resonance imaging requires a subject to remain relatively still to achieve effective magnetic resonance imaging for the corpus callosum of the fetus. Thus, conventional imaging techniques cannot provide an effective imaging method for obtaining the corpus callosum volume.

SUMMARY

In view of this, the present disclosure proposes a measurement method capable of precisely measuring the corpus callosum volume of a fetus by means of magnetic resonance images.

One embodiment of the present disclosure provides a method for measuring the corpus callosum volume of a fetus by means of magnetic resonance imaging, the method comprising: acquiring a scanogram of a fetus to be detected by means of magnetic resonance imaging; determining a detection area P according to the corpus callosum position of the fetus in the scanogram, the detection area P containing the corpus callosum of the fetus; performing magnetic resonance scanning on the detection area to obtain a diffusion weighted image of the detection area, with a gradient direction during the magnetic resonance scanning being taken only in a direction vertical (e.g. orthogonal, perpendicular, or normal) to an extending direction of fiber bundles of the corpus callosum; cropping a fetal head image in the diffusion weighted image; applying a predetermined threshold to the fetal head image to obtain an image having pixels associated with a logical high value of the brightness in the image that are greater than the threshold; and performing image processing (e.g. "spotlight" processing or other image processing such as e.g. blob detection or cluster detection) on the image with pixels associated with the logical high signal values, with the maximum region (e.g., the largest region or "cluster") therein as the corpus callosum, and calculating the sum of voxel dimensions associated with the largest region as the corpus callosum volume.

In the method for measuring the corpus callosum volume of a fetus, the head position of the fetus and the detection area are determined in the scanogram by using a deep learning model or a machine learning model.

In the method for measuring the corpus callosum volume of a fetus, a fetal head image is cropped in the diffusion weighted image by using a deep learning model or a machine learning model.

In the method for measuring the corpus callosum volume of a fetus, a histogram of the fetal head image is obtained, a predetermined threshold is applied to the histogram, the fetal head image is converted into a binary image, and image processing is performed on the binary image obtained after conversion (e.g. binarization).

In the method for measuring the corpus callosum volume of a fetus, the scanograms include scanograms at three positions, including a sagittal view, a coronal view and a transverse view, and the detection area is a flat-plate area that can contain the corpus callosum in the scanograms at the three positions.

In the method for measuring the corpus callosum volume of a fetus, the diffusion weighted image is an image based on single-shot echo planar imaging.

In the method for measuring the corpus callosum volume of a fetus, the diffusion weighted image is obtained by imaging during a single breath-hold of the maternal body of the fetus to be detected.

Another embodiment of the present disclosure provides a magnetic resonance imaging apparatus, which measures the corpus callosum volume of a fetus by using any method described above for measuring the corpus callosum volume of a fetus by means of magnetic resonance imaging.

According to the method for measuring the corpus callosum volume of a fetus by means of magnetic resonance imaging in the present disclosure, it is possible to precisely and quantitatively measure the corpus callosum volume of a fetus in a motion state from time to time, thereby providing an auxiliary determination basis for abnormalities of the corpus callosum of fetuses. In particular, when an artificial intelligence model such as a deep learning is used, it is possible to further achieve the fully automatic, precise, and quantitative measurement of the corpus callosum volume of fetuses, thereby saving on time required for measurement and improving the utilization efficiency of magnetic resonance imaging apparatuses.

BRIEF DESCRIPTION OF THE DRAWINGS/FIGURES

The above and other features and advantages of the present disclosure will be more apparent to those of ordinary skill in the art from the detailed description of preferred embodiments of the present disclosure with reference to the accompanying drawings, in which.

DETAILED DESCRIPTION

In order to make the object, technical solutions, and advantages of the present disclosure more apparent, the present disclosure will be further described in detail by way of embodiments hereinafter.

One embodiment of the present disclosure provides a measurement method for obtaining the corpus callosum volume of a fetus by means of magnetic resonance imaging. According to this method, the corpus callosum volume of a fetus can be obtained, thereby providing auxiliary determination for abnormalities of corpus callosum.

Figure 1:
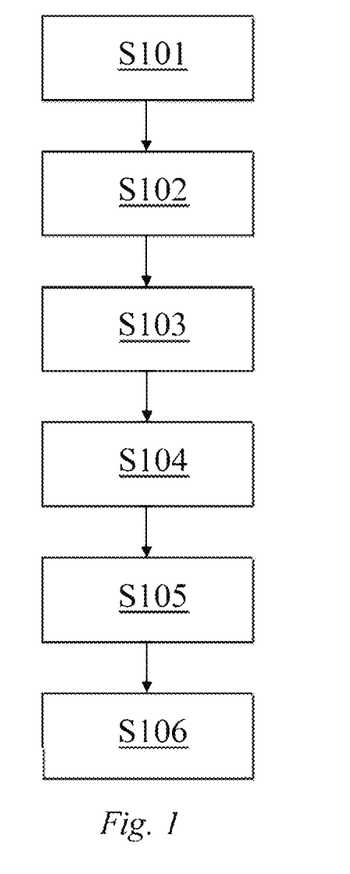
FIG. 1 shows a method for measuring the corpus callosum volume of a fetus by means of magnetic resonance imaging according to an embodiment of the present disclosure.
Figure 2A:
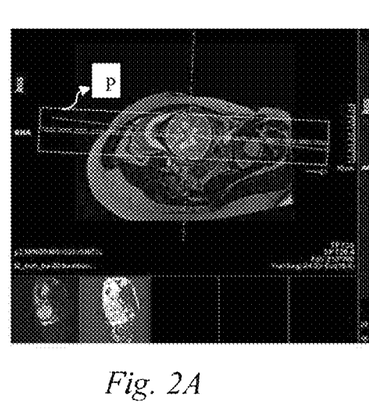
FIG. 2A shows a coronal scanogram of a fetus during magnetic resonance imaging and the position of a detection area P (a rectangular box in the figure) in the scanogram according to an embodiment of the present disclosure.
Figure 2B:
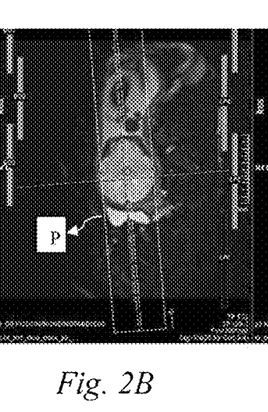
FIG. 2B shows a transverse scanogram of the fetus and the position of the detection area P in the scanogram according to an embodiment of the present disclosure.
Figure 2C:
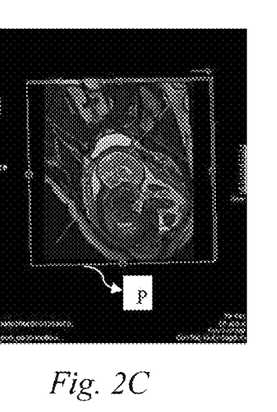
FIG. 2C shows a sagittal scanogram of the fetus and the position of the detection area P in the scanogram according to an embodiment of the present disclosure.

FIG. 1 shows a method for measuring the corpus callosum volume of a fetus by means of magnetic resonance imaging according to the present disclosure. FIG. 2A shows a coronal scanogram of a fetus during magnetic resonance imaging and the position of a detection area P (a rectangular box in the figure) in the scanogram. FIG. 2B shows a transverse scanogram of the fetus and the position of the detection area P in the scanogram. FIG. 2C shows a sagittal scanogram of the fetus and the position of the detection area P in the scanogram.

Figure 3A:
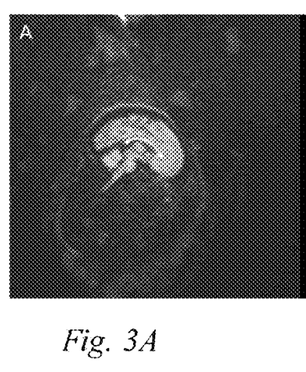
FIG. 3A shows a diffusion weighted image obtained by magnetic resonance scanning on the detection area P according to an embodiment of the present disclosure.
Figure 3B:
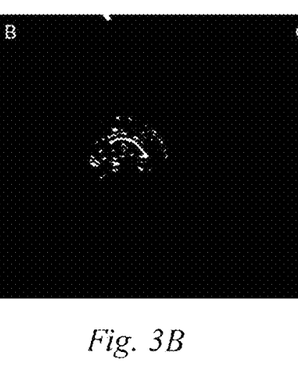
FIG. 3B shows a binary image of a fetal head image converted by applying a predetermined threshold to the fetal head image according to an embodiment of the present disclosure.

The method for measuring the corpus callosum volume of a fetus according to the present disclosure will be described below with reference to FIGS. 1-3. First, as shown in FIG. 1, the measurement method comprises the following:

In step S101, scanograms of a fetus to be detected are acquired by means of magnetic resonance imaging.

As an example, magnetic resonance scanning may be performed on a body to be detected using sequences such as TrueFISP and T2-HASTE to obtain the scanograms of the fetus. As shown in FIG. 2, the scanograms include scanograms at three positions, including a sagittal view, a coronal view, and a transverse view. FIG. 2A represents the coronal scanogram of the fetus, FIG. 2B represents the transverse scanogram of the fetus, and FIG. 2C represents the sagittal scanogram of the fetus.

In step S102, a detection area P is determined according to the corpus callosum position of the fetus in the scanogram, the detection area P containing the corpus callosum of the fetus.

In this embodiment, as shown in FIG. 2, a rectangular area (rectangular areas shown in FIGS. 2A, 2B and 2C, respectively) is set in a manner in which the three scanograms can respectively contain the corpus callosum of the fetus, so as to determine the three-dimensional detection area P used for magnetic resonance scanning. It can be seen that the detection area P is a flat-plate area that contains the corpus callosum.

In this example, the position of the fetal brain and the position of the corpus callosum detection area P may be determined by means of the deep learning or machine learning model, so as to achieve fully automatic detection of the corpus callosum volume of the fetus. Hereinafter, with reference to FIG. 4, a fetal brain mask and a mask representing the corpus callosum detection area P that are used for a deep learning model or a machine learning model according to the present disclosure will be described in detail.

Figure 4:
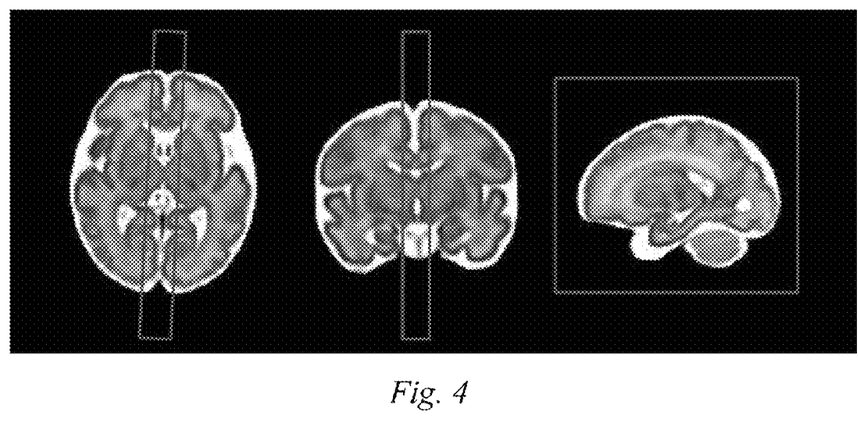
FIG. 4 shows schematic diagrams of samples marked with a fetus brain mask and a detection area mask that are used for a deep learning model or a machine learning model according to an embodiment of the present disclosure, with a coronal scanogram, a transverse scanogram, and a sagittal scanogram being sequentially shown from left to right.

Specifically, when the fetal brain and the corpus callosum detection area P are automatically acquired based on the deep learning model such as TensorFlow or ImageNet, for instance, or based on the machine learning model such as landmark based on an automatic alignment algorithm, as shown in FIG. 4, coronal scanograms, transverse scanograms, and sagittal scanograms (arranged from left to right with reference to FIG. 4) of any suitable number (e.g. 100-500) of infants during magnetic resonance imaging may be first acquired. Each scanogram may be manually marked with a mask for the fetal brain (an area in a white contour in FIG. 4) and a mask for the corpus callosum detection area P (a rectangular box), with the mask for the corpus callosum detection area P capable of respectively containing the corpus callosum in an area range of the mask in the three scanograms. The image data may be used to train the deep learning model or the machine learning model so that the deep learning model or the machine learning model can automatically identify and determine the position of the fetal brain and the position of the detection area P in magnetic resonance images. In this embodiment, as shown in FIG. 2, the deep learning or machine learning model trained as above automatically locates the fetal brain in the three scanograms of the detected fetus and determines the corresponding position of the detection area P containing the corpus callosum.

Certainly, in addition to applying the deep learning or machine learning model so as to automatically detect the position of the fetal brain and the detection area P, the position of the fetal brain and the detection area P may also be manually marked in the three scanograms of the detected fetus in practical.

In step S103, magnetic resonance scanning is performed on the detection area P containing the corpus callosum to obtain a diffusion weighted image of the detection area P, with a gradient direction during the magnetic resonance scanning being taken only in a direction orthogonal or normal to an extending direction of fiber bundles of the corpus callosum.

After the detection area P is determined, magnetic resonance imaging may be performed using a sequence based on single-shot echo planar imaging (SS-EPI). Because the diffusion direction is consistent with the applied gradient direction, the gradient direction needs only be taken in the direction orthogonal or normal to the extending direction of fiber bundles of the corpus callosum during the magnetic resonance scanning FIG. 3A shows a diffusion weighted image obtained by magnetic resonance scanning on the detection area P in this embodiment. As shown in FIG. 3A, the corpus callosum is represented with pixels represented as having a "high" logical brightness value in the obtained magnetic resonance image. Moreover, to obtain an ideal image, it is preferable that the diffusion weighted imaging mentioned above is performed during a single breath-hold of the maternal body of the detected fetus. In addition, although the single-shot echo planar imaging is exemplarily used, other methods can be employed, as long as a diffusion weighted image can be obtained.

In step S104, a fetal head image is cropped from the diffusion weighted image obtained in step S103 described above.

The diffusion weighted image obtained in step S103 described above further includes, as shown in FIG. 3A, a partial image of the maternal body of the fetus in addition to the detection area P. Here, for further convenient processing, the fetal head image in the diffusion weighted image may be automatically cropped by using the trained deep learning or machine learning model described above. Of course, the fetal head image may also be cropped manually in this step.

In step S105, a predetermined threshold is applied to the fetal head image obtained in step S104 described above so as to obtain the image having pixels represented with logical high signal values, i.e. the brightness value of each pixel in the image is greater than the selected predetermined threshold.

In this embodiment, a histogram of the fetal head image may be obtained, and the predetermined threshold applied to the histogram, the brightness value greater than the threshold being set to be a logical high value (e.g. 1), and the brightness value less than the threshold is set to be a logical low value (e.g. 0), thereby converting the fetal head image into a binary image (i.e. via binarization of the image). FIG. 3B shows a binary image of a fetal head image converted by applying a predetermined threshold to the fetal head image, with a white part representing pixels associated with the logical high signal values, and a black part representing pixels associated with the logical low signal values. As shown in FIG. 3B, in this binary image, in addition to the largest region representing the corpus callosum being displayed as pixels with logical high signal values, there are other smaller groups of pixels also associated with logical high brightness signal values, which are generated due to the signal-to-noise ratio of magnetic resonance signals or fibers of other anatomical tissues in the head.

In step S106, image processing (e.g. spotlight processing, blob detection, cluster detection, etc.) is performed on the binarized image including only pixels having the logical high signal values obtained in step S105, with the maximum or largest region or spot therein being identified as the corpus callosum, and the sum of associated voxel dimensions in the maximum or largest region being calculated as the corpus callosum volume.

Figure 3C:
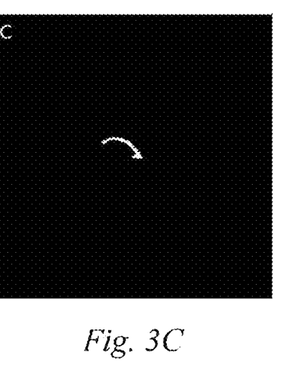
FIG. 3C shows an image of the largest region as the corpus callosum, obtained after image processing of the binary image according to an embodiment of the present disclosure.

FIG. 3C shows an image of the maximum or largest region as the corpus callosum, obtained after image processing for the binary image obtained in step S105 described. As shown in FIG. 3C, after the image processing for the pixels having associated logical high signal values connected in space in the binary image, the maximum or largest region representing the corpus callosum is obtained, and then the sum of voxel dimensions associated with the pixels having the associated logical high signal values of the maximum or largest region is calculated as the corpus callosum volume.

In the embodiment described above, it is not necessary to perform image processing after converting the fetal head image into the binary image. It is also possible to apply a predetermined threshold to the fetal head image, discard the pixels associated with a brightness value less than the threshold, and perform image processing for pixels having logical high values indicating a brightness value greater than the predetermined threshold.

The present disclosure further provides a magnetic resonance imaging apparatus using the method for measuring the corpus callosum volume of a fetus described above.

According to the method for measuring the corpus callosum volume of a fetus by means of magnetic resonance imaging in the present disclosure, it is possible to precisely and quantitatively measure the corpus callosum volume of a fetus in a motion state from time to time, thereby providing an auxiliary determination basis for abnormalities of corpus callosum of fetuses. In particular, when an artificial intelligence model such as a deep learning is used, it is possible to further achieve the fully automatic, precise and quantitative measurement of the corpus callosum volume of fetuses, thereby saving on time required for measurement and improving the utilization efficiency of magnetic resonance imaging apparatuses.

FIG. 4 illustrates an example magnetic resonance imaging device, in accordance with an embodiment of the present disclosure. The magnetic resonance imaging device as shown in FIG. 4 may also be referred to as a magnetic resonance imager or magnetic resonance imaging system. This comprises, as known in principle, a main magnet unit 6 (e.g. a magnetic data acquisition unit or scanner) that defines a patient receiving space 7 into which a patient can be moved by means of a patient support 8 (not shown in further detail here). Surrounding the patient support 8, a high frequency arrangement of the magnetic resonance imaging device 5 and a gradient coil arrangement of the magnetic resonance imaging device can be provided and, for the sake of clarity, these are also not shown.

The magnetic resonance imaging apparatus 5 may be controlled by a control device 10, which may also be referred to as a control computer, control circuitry, or a control unit. The control device 10 is configured to communicate with and/or control one or more components of the magnetic resonance imaging device 5. In various aspects, the control device 5 may do so to perform one or more methods according to the present disclosure, such as the method as shown and described with reference to FIG. 1. The control device 10 may be implemented, for example, as one or more computer processors. Thus, the various components of the control device 10 as discussed below may be implemented as separate processors, or their respective functions shared among one or more processors of the control device 10. The various functions of the components of the control device 10, which are discussed directly below, may be achieved via any suitable combination of one or more hardware processors, software, or a combination of both. Moreover, one or more functions as described herein with reference to the magnetic resonance imaging apparatus 5 and/or the control device 10 may be additionally or alternatively performed via any other suitable computing component that may be separate from the components shown in FIGS. 4 and 5 (e.g., a machine learning algorithm executed by a computer in communication with the magnetic resonance imaging apparatus 5 and/or the control device 10).

Figure 5:
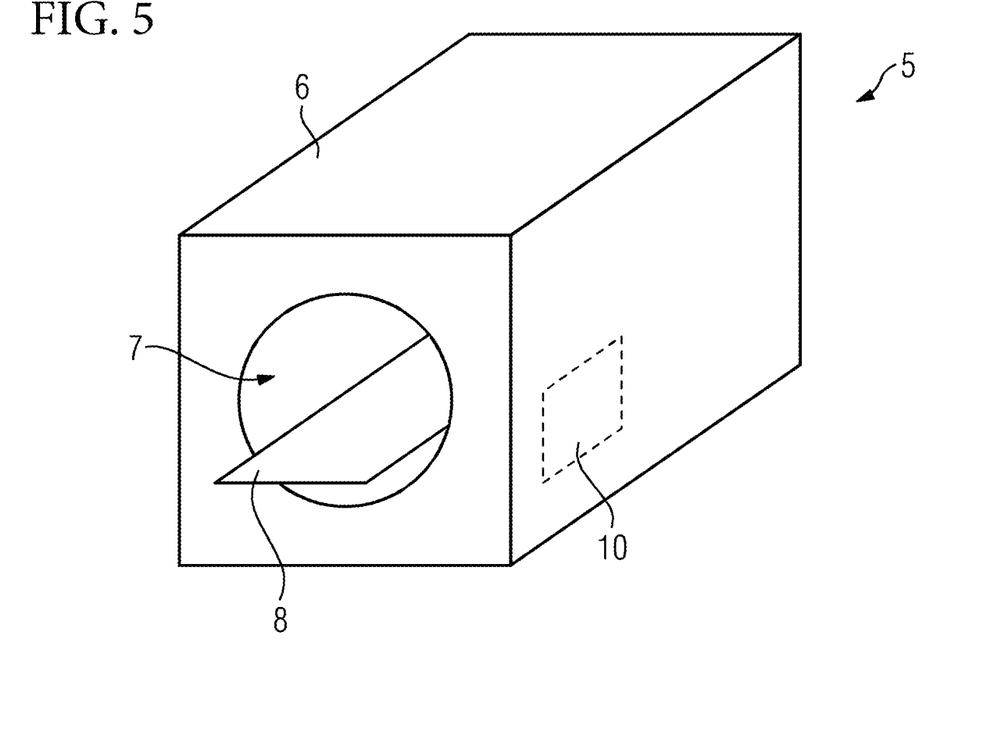
FIG. 5 illustrates an example magnetic resonance imaging device, in accordance with an embodiment of the present disclosure.
Figure 6:
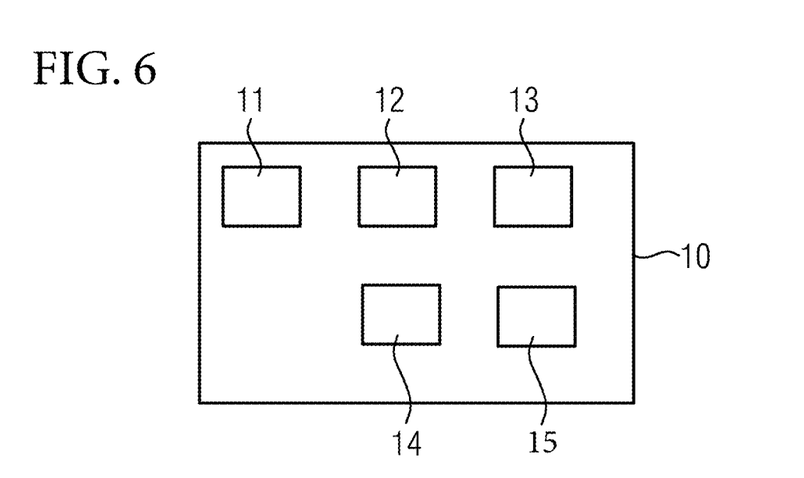
FIG. 6 illustrates an example functional structure of a control device of the magnetic resonance imaging device shown in FIG. 5, in accordance with an embodiment of the present disclosure.

FIG. 5 shows the functional structure of the control device 10. The control device 10 comprises scanogram acquisition circuitry 11 to control the magnetic resonance imaging device 5 to acquire scanograms of a fetus by means of magnetic resonance imaging, in this example as discussed in step S101 of FIG. 1. The control device 10 also includes region detection circuitry 12 configured to detect an area P according to the corpus callosum position of the fetus in the acquired scanogram, in this example as discussed in step S102 of FIG. 1.

The control device 10 also includes magnetic resonance scanning control circuitry 13 configured to control the magnetic resonance imaging device 5 to perform magnetic resonance scanning on the detection area P containing the corpus callosum to obtain a diffusion weighted image of the detection area P, in this example as discussed in step S103 of FIG. 1. Furthermore, the control device 10 also includes image processing circuitry 14 configured to crop a fetal head image from the diffusion weighted image, apply a predetermined threshold to the fetal head image, and to perform image processing in the cropped and binarized fetal head image (e.g. spotlight processing, blob detection, cluster detection, etc.) to identify the largest region as the corpus callosum, and to calculate the sum of associated voxel dimensions in the largest region as the corpus callosum volume, in this example as discussed in steps S104, S105, and S106 of FIG. 1.

The control device 10 may also include one or more memories 15, such as non-transitory computer-readable mediums, for example. The one or more memories 15 may be configured as any suitable type of storage mediums such as volatile or non-volatile storage devices, and may form part of the control device 10 or otherwise be accessed by the control device 10 (e.g., via a network), and thus be external to the control device 10 (not shown). Aspects include any of the methods being performed additionally or alternatively via executable instructions stored in the one or more memories 15, which may be executed by one or more components of the control device 10 and/or the magnetic resonance imaging device 5 (e.g., via one or more processors).

The above descriptions are merely preferred embodiments of the present disclosure but not intended to limit the present disclosure, and any modifications, equivalent replacements, improvements, etc. made within the spirit and principle of the present disclosure should be included within the scope of protection of the present disclosure.

Moreover, although the embodiments as described herein specify that the gradient direction is oriented orthogonal or normal to an extending direction of fiber bundles of the corpus callosum, this is by way of example and not limitation. The embodiments as described herein may utilize additional or alternate orientations of the magnetic gradient in this context depending upon the particular application or desired results. For instance, the magnetic gradient may alternatively be oriented parallel to an extending direction of fiber bundles of the corpus callosum.

What is claimed is:

1. A method for measuring a corpus callosum volume of a fetus via magnetic resonance imaging, the method comprising:
    acquiring at least one scanogram of the fetus;
    determining a detection area according to a position of a corpus callosum of the fetus in the at least one scanogram, the detection area containing the corpus callosum of the fetus;
    performing magnetic resonance scanning on the detection area to obtain a diffusion weighted image of the detection area, the magnetic resonance scanning being performed using a gradient direction that runs in a direction orthogonal to an extending direction of fiber bundles of the corpus callosum of the fetus;
    cropping a fetal head image of the fetus from the diffusion weighted image;
    applying a predetermined threshold to the fetal head image to obtain a converted fetal head image including pixels having a brightness value greater than the predetermined threshold;
    performing image processing of the converted fetal head image to identify a largest region in the converted fetal head image as the corpus callosum of the fetus; and
    calculating a sum of voxel dimensions associated with the largest region in the fetal head image as the corpus callosum volume of the fetus.

2. The method as claimed in claim 1, wherein a head position of the fetus and the detection area containing the corpus callosum of the fetus are determined in the at least one scanogram of the fetus using a deep learning model or a machine learning model.

3. The method as claimed in claim 1, wherein the fetal head image is cropped from the diffusion weighted image using a deep learning model or a machine learning model.

4. The method as claimed in claim 1, further comprising:
    applying the predetermined threshold to a histogram of the fetal head image to convert the fetal head image to thereby obtain, as the converted fetal head image, a binary image.

5. The method as claimed in claim 1, wherein the at least one scanogram of the fetus is from among a set of scanograms of the fetus that include a sagittal scanogram of the fetus, a coronal scanogram of the fetus, and a transverse scanogram of the fetus, and
    wherein the detection area contains the corpus callosum of the fetus in each of the set of scanograms.

6. The method as claimed in claim 1, wherein the diffusion weighted image is an image based on single-shot echo planar imaging.

7. The method as claimed in claim 1, wherein the diffusion weighted image is obtained by imaging during a single breath-hold.

8. A magnetic resonance imaging device for measuring a corpus callosum volume of a fetus via magnetic resonance imaging, comprising:
    a patient space configured to receive a patient including a fetus; and
    a control computer configured to control the magnetic resonance device to:
        acquire at least one scanogram of the fetus;
        determine a detection area according to a position of a corpus callosum of the fetus in the at least one scanogram, the detection area containing the corpus callosum of the fetus;
        perform magnetic resonance scanning on the detection area to obtain a diffusion weighted image of the detection area, the magnetic resonance scanning being performed using a gradient direction that runs in a direction orthogonal to an extending direction of fiber bundles of the corpus callosum of the fetus;

crop a fetal head image of the fetus from the diffusion weighted image;

apply a predetermined threshold to the fetal head image to obtain a converted fetal head image including pixels having a brightness value greater than the predetermined threshold;

perform image processing of the converted fetal head image to identify a largest region in the converted fetal head image as the corpus callosum of the fetus; and calculate a sum of voxel dimensions associated with the largest region in the fetal head image as the corpus callosum volume of the fetus.

9. The magnetic resonance imaging device as claimed in claim 8, wherein control computer is configured to control the magnetic resonance device to apply the predetermined threshold to a histogram of the fetal head image to convert the fetal head image to thereby obtain, as the converted fetal head image, a binary image.

10. The magnetic resonance imaging device as claimed in claim 8, wherein the at least one scanogram of the fetus is from among a set of scanograms of the fetus that include a sagittal scanogram of the fetus, a coronal scanogram of the fetus, and a transverse scanogram of the fetus, and wherein the detection area contains the corpus callosum of the fetus in each of the set of scanograms.

11. The magnetic resonance imaging device as claimed in claim 8, wherein the diffusion weighted image is an image based on single-shot echo planar imaging.

12. The magnetic resonance imaging device as claimed in claim 8, wherein the diffusion weighted image is obtained by imaging during a single breath-hold.

13. A non-transitory computer readable medium having instructions stored thereon that, when executed by one or more processors associated with a magnetic resonance imaging device, cause the magnetic resonance imaging device to measure a corpus callosum volume of a fetus by:

acquiring at least one scanogram of the fetus;

determining a detection area according to a position of the corpus callosum of the fetus in the at least one scanogram, the detection area containing the corpus callosum of the fetus;

performing magnetic resonance scanning on the detection area to obtain a diffusion weighted image of the detection area, the magnetic resonance scanning being performed using a gradient direction that runs in a direction orthogonal to an extending direction of fiber bundles of the corpus callosum;

cropping a fetal head image from the diffusion weighted image;

applying a predetermined threshold to the fetal head image to obtain a converted fetal head image including pixels having a brightness value greater than the predetermined threshold;

performing image processing of the converted fetal head image to identify a largest region in the converted fetal head image as the corpus callosum of the fetus; and calculating a sum of voxel dimensions associated with the largest region in the fetal head image as the corpus callosum volume of the fetus.

14. The non-transitory computer readable medium as claimed in claim 13, wherein the instructions, when executed by one or more processors associated with a magnetic resonance imaging device, cause the magnetic resonance imaging device to apply the predetermined threshold to a histogram of the fetal head image to convert the fetal head image to thereby obtain, as the converted fetal head image, a binary image.

15. The non-transitory computer readable medium as claimed in claim 13, wherein the at least one scanogram of the fetus is from among a set of scanograms of the fetus that include a sagittal scanogram of the fetus, a coronal scanogram of the fetus, and a transverse scanogram of the fetus, and wherein the detection area contains the corpus callosum of the fetus in each of the set of scanograms.

16. The non-transitory computer readable medium as claimed in claim 13, wherein the diffusion weighted image is an image based on single-shot echo planar imaging.

17. The non-transitory computer readable medium as claimed in claim 13, wherein the diffusion weighted image is obtained by imaging during a single breath-hold.

* * * * *